United States Patent [19]

Russell, Jr. et al.

[11] Patent Number: 4,675,150
[45] Date of Patent: Jun. 23, 1987

[54] APPARATUS FOR NEUTRON-CAPTURE TUMOR THERAPY

[75] Inventors: John L. Russell, Jr., Alpharetta; Denise J. Noonan, Atlanta, both of Ga.

[73] Assignee: Theragenics Corporation, Atlanta, Ga.

[21] Appl. No.: 653,316

[22] Filed: Sep. 24, 1984

Related U.S. Application Data

[62] Division of Ser. No. 390,941, Jun. 22, 1982.

[51] Int. Cl.$^4$ .............................................. G21C 23/00
[52] U.S. Cl. .................................... 376/340; 128/1.1; 250/518.1
[58] Field of Search ...................... 376/158, 340, 346; 250/518.1; 128/1.1

[56] References Cited

U.S. PATENT DOCUMENTS

| 3,148,280 | 9/1964 | Kleber et al. | 250/518.1 |
| 3,280,329 | 10/1966 | Harmer et al. | 376/340 |
| 3,372,275 | 3/1968 | Kocher | 250/518.1 |
| 3,389,258 | 6/1968 | Reed et al. | 250/518.1 |

FOREIGN PATENT DOCUMENTS 122720  9/1980  Japan ................................... 128/1.1

OTHER PUBLICATIONS

Hatanaka et al., "A Revised Boron-Neutron Capture Therapy for Malignant Brain Tumours", Z. Neurol. 204, pp. 309-332, 1973.
Zamenhof et al., "Boron Neutron Capture Therapy for the Treatment of Cerebral Gliomus . . . ," Medical Physics, vol. 2, No. 2, pp. 47-60, 1975.
Hatanaka et al., "Boron-Neutron Capture Therapy in Relation to Immunotherapy, " Acta Neurochirurgica 42, pp. 55-72, 1978.
Brownell et al., "Boron Neutron Capture Therapy," Modern Trends in Radiotherapy I, Deley & Wood (eds) Butterworths, London, pp. 205-222, 1978.
Zamenhof, R. G. et al., "Boron Neutron Capture Therapy for the Treatment of Cerebral Gliomas I: Theoretical Evaluation of the Efficacy of Various Neutron Beams", Medical Physics, vol. 2, No. 2, Mar./Apr. 1975, pp. 47-60.
McDonald, J. et al., "Clinical Oncology for Medical Students and Physicians", Univ. of Rochester School of Med. and Dent., 1974, pp. 343-358.
Acta Radiologia (Supplement 170) pp. 50-53, 1958.
Fairchild, R. G., "Development and Dosimetry of an 'Epithermal' Neutron Beam for Possible Use in Neutron Capture Therapy I. 'Epithermal' Neutron Beam Development" Phys. Med. Biol. vol. 10, No. 4, pp. 491-504 (1965).

Primary Examiner—Deborah L. Kyle
Assistant Examiner—Richard L. Klein
Attorney, Agent, or Firm—Fitch, Even, Tabin & Flannery

[57] ABSTRACT

A tumorous patient is injected with a compound including an element that accumulates in tumors and that has an isotope which emits an alpha particle in a neutron capture reaction. The patient is positioned in front of a radiation beam that has been filtered to remove most neutrons having energies above 30 KeV and most thermal neutrons, leaving predominantly epithermal neutrons which are moderated to a thermal level by outer layers of tissue and are captured by the incorporated isotope.

A radiation beam having neutrons with a wide distribution of energies is filtered with aluminum, sulfur and argon filters, whose cross sections complement each other in providing a beam with energies predominantly in the epithermal range. The filter mass attenuates the gamma radiation. Beams with lower ratios of undesirable gamma radiation to epithermal beam intensity can be attained with filter combinations which include liquid argon. A poor geometry filter of bismuth or lead can also improve the gamma to neutron ratio. Preferably the beam is filtered through a thermal neutron filter as well.

14 Claims, 4 Drawing Figures

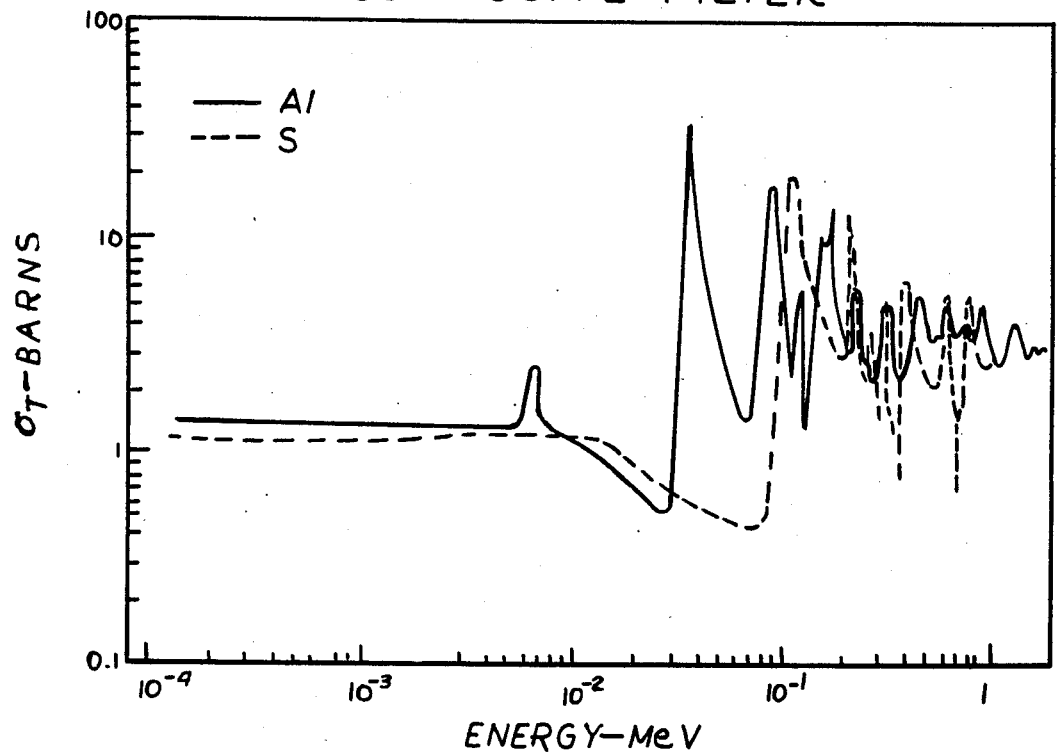
FIG.1. TOTAL CROSS SECTION OF COMPOSITE FILTER
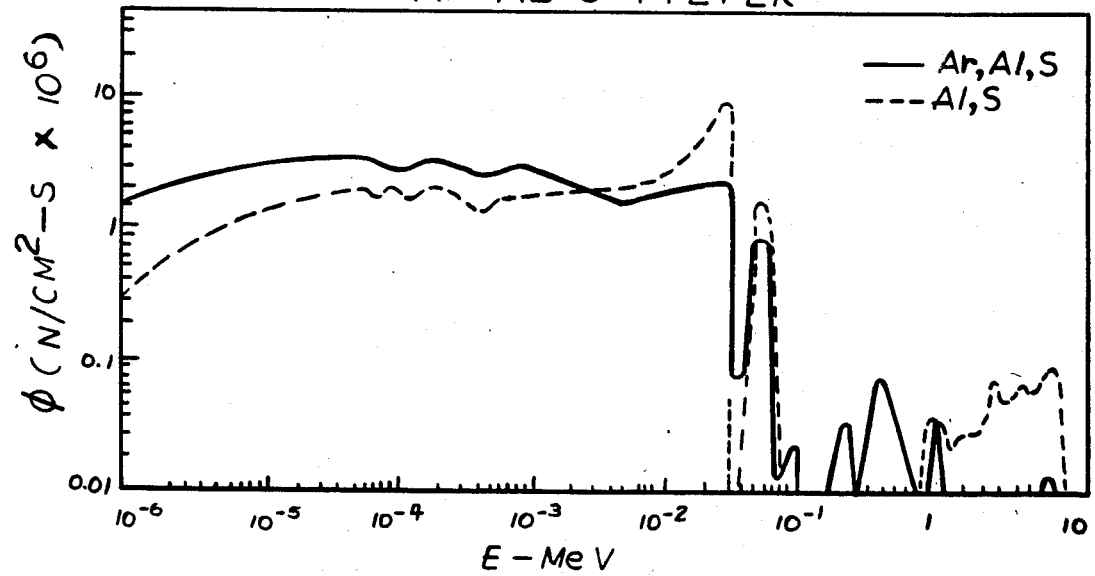
FIG.2. NEUTRON TRANSMISSION SPECTRUM AR-AL-S FILTER

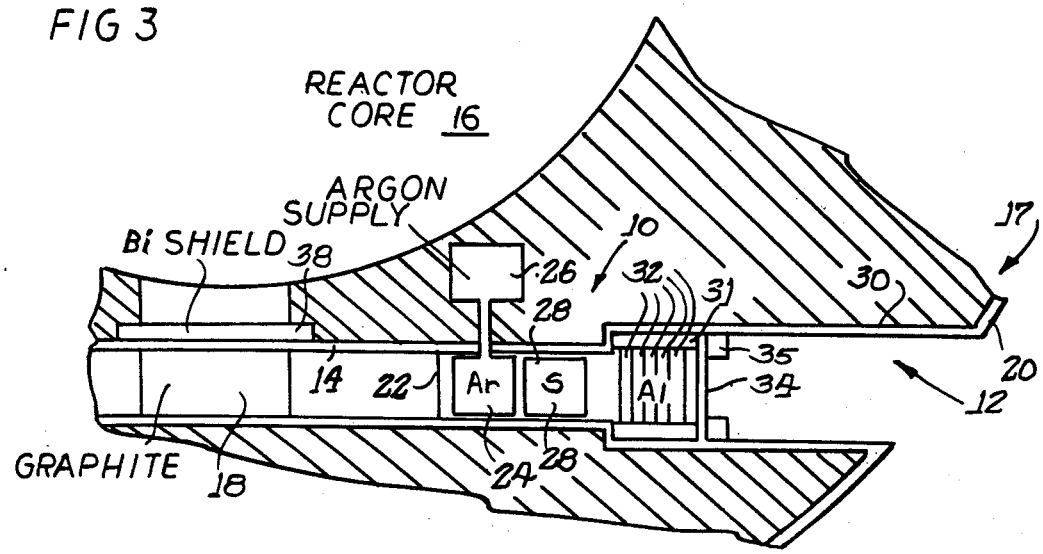
FIG 3
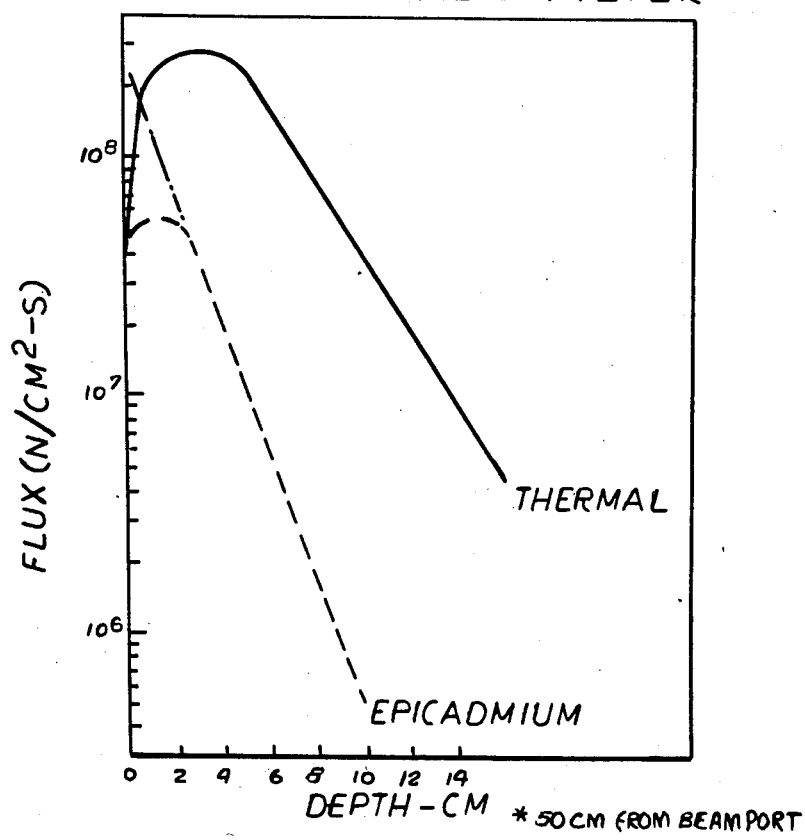
FIG. 4. THERMAL FLUX GENERATED IN A HEAD PHANTOM* AL-S FILTER
*50 CM FROM BEAM PORT

APPARATUS FOR NEUTRON-CAPTURE TUMOR THERAPY

This is a division of application Ser. No. 390,941, filed June 22, 1982.

The present invention is related to apparatus for treating tumors, and more particularly to apparatus for providing a neutron beam particularly advantageous for neutron-capture tumor therapy.

BACKGROUND OF THE INVENTION

An ever increasing number of people are being afflicted with cancer. Conventional treatments such as surgery, radiation therapy and chemotherapy have been extremely successful in certain cases; in other instances, much less so. A much less familiar, alternative form of cancer therapy known as Boron Neutron-Capture Therapy (BNCT) has been used to treat certain tumors for which the general methods are ineffective. In particular, it has been used to treat *Glioblastoma multiformae*, a highly malignant, invasive form of brain cancer. In this therapy, a patient is injected with a boron compound highly enriched in $B^{10}$. The boronated compound concentrates preferentially in the brain tumor, while the action of the blood-brain barrier prevents its entry into the healthy surrounding tissues. The patient's head is then irradiated with a beam of thermal neutrons that are captured by the boron concentrated in the tumor according to the $B^{10}(n,\alpha)Li^7$ reaction. The tumor is thus irradiated with high LET alpha and Li particles whose range in tissue is about $10\mu$, or the diameter of an average cell. Therefore, a very localized, specific reaction takes place whereby the tumor receives a large radiation dose, compared to that received by the surrounding healthy tissue, from the transit of the thermal neutrons.

Clinical trials of BNCT were conducted in the 1950's at Brookhaven by Farr; Farr, L. E., *Applications, of Radioisotopes & Radiation in the Life Sciences*, U.S. Gov'n't Printing Office, March 1961; Sweet, Robertson and Stickley et al, *Amer. J. of Roentgenology*, 73, 279-293, 1954; and in the 1960's by Brownell, Sweet, and Soloway working at MIT; Asbury, A. K., et al, *J. of Neuropath & Expt. Neurol.*, 31, 278-303, 1972; but with limited success.

Subsequent studies revealed two major problems. First of all, the boron compound was present in the skin and the blood vessels at concentrations equivalent to or greater than that in the tumor itself, resulting in severe damage to the blood vessel walls and the scalp directly in line with the treatment port. However, the problem appears to have been solved with the development of a low toxicity boron compound, $Na_2B_{12}H_{11}SH$. Tumor-to-blood boron concentration ratios of as high as 3:1 have been attained 12-24 hours after injection, Hatanaka, H., *J. of Neurol.*, 207, 81-94, 1975.

The primary physical problem encountered was the rapid attenuation of the thermal neutron flux, preventing effective treatment of deep-seated tumors. A large proportion of the thermal neutrons never reach the tumor, but instead damage normal tissue. As a possible solution, substitution of the thermal beam by an epithermal beam has been proposed.

The rational for epithermal (intermediate) neutrons is that these neutrons pass through the outer layers of tissue losing energy in the process. After sufficient attenuation by tissues, the epithermal neutrons are slowed to the thermal energy range where they are subject to a high probability of capture by the $B^{10}$. In order that an epithermal beam may be used for neutron-capture tumor therapy, a relatively safe epithermal beam must be provided. That is, an epithermal beam must be provided which has sufficiently low fluxes of destructive fast neutrons, thermal neutrons and gamma rays. Several attempts have been made at constructing an epithermal beam by scattering from a thin hydrogeneous material or by filtering a thermalized beam with Cd or $Li^6$, Frigerio, N. A., *Phys. in Med. & Biol.*, 6, 541-549, 1962, Fairchild, R. G., *Phys. in Med. & Biol.* 10, 491-504, 1965. However, either the gamma and/or fast neutron contamination was too high for therapeutic purposes, or the epithermal flux was too low. The need continues for a satisfactory means for providing an epithermal beam suitable for BNCT.

BRIEF DESCRIPTION OF THE DRAWINGS

FIG. 1 is a log-log graph showing the neutron capture cross sections of aluminum and sulfur;

FIG. 2 is a log-log graph showing the neutron transmission spectrum of Al-S and Ar-Al-S filter systems;

FIG. 3 is a diagrammatic illustration of a nuclear reactor and neutron filter arrangement embodying various features of the invention; and FIG. 4 is a semi-log graph showing the thermal and epicadmium fluxes at various depths in a head phantom radiated through an Al-S filter system.

DETAILED DESCRIPTION OF THE PREFERRED EMBODIMENTS

In accordance with the present invention, apparatus is provided for treating a patient having a tumor, such as a brain tumor, by injecting the patient with a compound that selectively accumulates in the tumor. The compound includes an element having an isotape that emits cell-destroying alpha particles upon neutron bombardment. A filtered neutron beam is provided which has a neutron flux greater than $10^7$ and preferably greater than about $5 \times 10^7$ n/cm² sec, a neutron energy distribution in which less than about 15% and preferably less than about 5% of the neutrons have energies above 30 KeV and a gamma radiation dosage within a medically acceptable range. The patient is positioned so that the tumor is in the path of the beam and is treated for an appropriate length of time. To provide a suitable beam of neutrons, a radiation beam, with neutrons having a wide energy distribution, is filtered through a filter system that includes some combination of aluminum, sulfur and argon filters, the neutron total cross sections of these materials being such that in combination they provide a neutron transmission "window" that selectively transmits epithermal neutrons. The filter system also attenuates gamma radiation. Preferably, additional thermal neutron filters are used to maintain the level of neutrons having energies below 0.5 eV to between 0.3 and about 30 percent of the total neutrons. Adjusting the ratio of thermal to epithermal neutrons changes the beam penetration to the proper depth for specific tumor location.

Neutron-capture therapy requires that the patient be injected with a compound that totally or at least partially accumulates in a tumor. The accumulating portion should include an element having an isotope, such as $B^{10}$ or $Li^7$, that captures neutrons and emits a cell-destroying alpha particle. For effective tumor destruction, the element should accumulate in the tumor so that the desired isotope is present in amounts of at least about 10 ppm and preferably at least about 50 ppm. The isotope-containing compound should be generally non-toxic; however, recognizing the seriousness of the threat posed by malignant tumors, the use of mildly toxic chemicals may be tolerated. Furthermore, it is highly desirable that the compound accumulates preferentially in the tumor so that the tumor will be destroyed without excessive damage to normal tissues, such as blood capillaries. As mentioned, hereinabove, $Na_2B_{12}H_{11}SH$ is the most suitable presently known compound, and the method of treatment will be hereinafter referred to as boron neutron-capture therapy (BNCT), although the invention is not limited to treatment using boron compounds and is intended to include neutron-capture therapy treatment using compounds having other alpha particle-emitting isotopes.

To accumulate the requisite amount of $Na_2B_{12}H_{11}SH$ in a tumor, generally a patient is injected with a dose of between about 2 g and about 30 g of $Na_2B_{12}H_{11}SH$ carried in a pharmaceutically acceptable medium between about 12 and about 24 hours prior to subjecting the patient to the filtered neutron beam. Alternatively, multiple doses of $Na_2B_{12}H_{11}SH$ might be administered over a period of a few days prior to radiation treatment. The patient is positioned in front of the beam of primarily epithermal neutrons so that the tumor is in the direct path of the beam. Typically, the patient's body is positioned between about 50 and 100 cm. from the beam port.

For the $B^{10}(n,\alpha)Li^7$ reaction, neutrons having energies of less than 0.5 eV, that is, primarily in the thermal energy range, are preferred because they have the highest probability of capture. However, directing a beam of thermal neutrons at a patient having a tumor is generally ineffective and may be harmful. Many tumors are well below the surface of the body, e.g., a brain tumor is typically between about 2 and about 10 cm. below the surface, and if a beam of thermal neutrons is directed at the tumor, it will be largely absorbed by the outer tissues before reaching the tumor, resulting in some destruction of the normal outer tissues and relatively little destruction of tumor material. On the other hand, neutrons having higher energies, i.e., epithermal neutrons will penetrate the outer tissue layers and be moderated during penetration reducing their energies to within the effective boron capture range, whereby at the depth of the tumor, a high flux of neutrons in the thermal range is provided. Neutrons having excessive energies, i.e., fast neutrons, are highly destructive to tissue. Hence, for purposes of destroying subsurface tumors, a beam highly enriched in intermediate or epithermal neutrons relative to both thermal and fast neutrons is most effective.

For purposes of this invention, epithermal neutrons will be considered to be those neutrons having energies in the 0.5 eV to 30 KeV range, i.e., the range which is felt to be most suitable for BNCT, and fast neutrons are considered to be those having energies above 30 KeV, i.e., those which have energies greater than desirable for treating humans. It is appreciated that for other purposes, neutrons having energies up to 100 KeV may be considered to be epithermal.

The selection of a combination of aluminum and sulfur filter elements for providing a beam of epithermal neutrons is a consequence of characteristics of their individual neutron absorption cross sections, which are measured in barns. The composite of the individual cross sections of Al and S provides a "window" which preferentially transmits epithermal neutrons while absorbing both thermal and fast neutrons. Aluminum and sulfur, like certain other elements, exhibit a deep minimum or "window" in their total cross sections just below a strong s-wave resonance. These minima are the result of the destructive interferences between the resonance and potential scattering contributions to the total cross section, as described by the Breit-Wigner formula. Depending upon the width and depth of this minimum, a semi-monoenergetic transmission beam can be produced if a thick enough filter is placed in a reactor beam port and if no other equally deep minima exist in the filter material. However, a beam filtered by a single element filter thick enough to provide such a semi-monoenergetic transmission beam would not have sufficient neutron flux for treating tumors.

FIG. 1 is a log-log graph showing the neutron absorption cross sections of aluminum (in solid line) and sulfur (in broken line), with the neutron capture in barns shown on the ordinate and the energy in MeV's shown on the abscissa. The minima in the Al and S cross sections are about 25 and 70 KeV respectively. It is to be noted that the deep minima of the S and Al neutron-capture cross sections lie in approximately the same epithermal energy region, complementing one another, while resonance peaks in the fast neutron region of one element cancel out many of the other minima of the other element. Also, to be noted is the fortuitous and unusual property shared by Al and S that their neutron-total cross sections in the fast region are greater than in the thermal or epithermal region. Therefore, by using a combination of Al and S filters, it is possible to obtain a high transmission flux in the epithermal region with minimal contamination from fast neutrons. A composite neutron transmission spectrum is drawn from the combination of aluminum and sulfur filters (FIG. 2 broken line). It can be seen that the great majority of the neutrons that pass through an Al-S filter have energies below 30 KeV.

To take advantage of the complementary cross sections of aluminum and sulfur, the thickness of the sulfur filter in the beam direction is preferably between about one-half and two times the thickness of the aluminum filter in the beam direction. These thicknesses apply to closely packed sulfur, such as may be provided by pouring molten sulfur into a container, the sulfur serving as a neutron filter in either its liquid or solid state. Various arrangements of filter elements may be advantageously employed; for example, the aluminum filter may be comprised of several aluminum plates, and the above-referred to thickness ratios are applicable to the total effective thicknesses of the filter portions of each element.

In addition to selectively removing fast neutrons from the radiation beam, a combined Al-S filter selectively removes thermal neutrons from the beam enhancing the relative proportions of epithermal neutrons; however, an Al-S filter transmits a higher proportion of thermal energy neutrons than is generally desired. An Al-S filter system also transmits substantial gamma radiation which is potentially destructive to body tissues. Hence, Al-S filters are preferably used in conjunction with thermal neutron filters and gamma radiation filters.

In accordance with a preferred aspect of the invention, a liquid argon filter in conjunction with aluminum and/or sulfur filters more selectively attenuates gamma radiation relative to neutron radiation. Argon has a neutron-absorbtion cross section similar to that of sulfur and aluminum, preferentially transmitting epithermal neutrons while blocking transmission of fast neutrons. Thus a filter system for BNCT may include a liquid argon filter in combination with either a sulfur filter or an aluminum filter but preferably with both a sulfur and an aluminum filter. The effectiveness of an Ar-Al-S filter system in providing a neutron beam with energies concentrated below 30 KeV is demonstrated by the solid line composite neutron transmission spectrum in FIG. 2. It should be noted that argon, in combination with aluminum and sulfur, almost entirely eliminates neutrons having energies greater than 1 MeV from the beam.

In order to most effectively to match a liquid argon filter with a sulfur-aluminum filter arrangement, the liquid argon in the beam direction typically has a thickness between about 1 and about 6 times the total thickness of the aluminum and/or sulfur filters in the beam direction; however, this may vary, depending upon other neutron absorbing or attenuating filter elements used in the system. It is preferred that the gamma filter be effective to reduce the gamma radiation dose rate to less than the biological equivalent of the neutron radiation dose rate.

Because a combination of aluminum and sulfur filters transmit a beam with a relatively high gamma radiation to neutron radiation ratio, it is necessary to further attenuate gamma radition relative to neutron radiation if high neutron doses are to be administered, as may be the case in an attempt to destroy a tumor with a single treatment. However, if a series of treatments in small dosage increments is contemplated, additional measures to selectively attenuate gamma radiation may not be necessary. Treatment using apparatus without additional gamma attenuation eliminates the practical problems of providing a liquid argon filter in close proximity to a heated nuclear reactor.

The gamma contribution is further reduced if a lead or bismuth shield is placed between the neutron source and the filter system. The lead or bismuth shield is placed against the core face is in what is known as "poor geometry" in which it will transmit neutrons, even though they are multiply scattered, while stopping gamma radiation. The Ar-Al-S filter is further from the core and in what is known in the trade as "good geometry" in which a single scattering of a neutron removes it from the beam.

Several elements are effective in selectively filtering low energy thermal neutrons from a neutron beam. Suitable elements for use as a thermal neutron filter include cadmium, lithium, boron and gadolinium. A thermal neutron filter may comprise one or more of these metals in elemental form or in a compound, such as boron carbide. Thermal neutron poisons, such as those listed above, are generally very effective, and the thermal neutron filter is typically very thin relative to the aluminum, sulfur and argon filters. The thermal neutron filter should be effective to reduce the thermal neutron flux to below about one percent of the total neutron flux, unless a specific tumor is located near the surface and a thermal neutron component is left unfiltered to reduce beam penetration.

The order of the aluminum, argon and sulfur filters is not considered particularly critical, although the order of argon-aluminum-sulfur, from the inner and to the outer end, appears to offer substantial advantage.

It is preferable to provide a thermal neutron filter inward of the argon, aluminum and sulfur filters to substantially eliminate thermal neutrons entering these filters. This reduces the total gamma radiation contribution by substantially eliminating the production of gamma radiation by thermal neutrons in these filters.

Referring now to the diagrammatic illustration in FIG. 3, a filter system 10 according to the invention is disposed in a tangential port 12 of a nuclear reactor 17. That is, the beam is comprised of neutrons scattered through a tube 14 disposed generally tangential to the core 16 of a nuclear reactor. The neutrons produced in the reactor core 16 are scattered by a plug 18 of material, such as graphite, positioned in the tube 14 adjacent the core. The tube 14 leads externally of the reactor 17, extending through biological shielding 20 that permits a patient to be positioned in close proximity to the reactor but effectively receive only the directed beam from the port 12.

The filter system 10, consisting of a series of filters, is disposed within the tube about halfway between the graphite plug 18 and its outer end, located within the region of the biological shielding 20. A thin plate 22 at the inner end absorbs thermal neutrons. This plate 22 may be a boral plate in which boron carbide is dispersed in aluminum sheets. Next in the series of filters is a chamber 24 containing liquid argion, with an external liquid argon supply system 26 continuously maintaining the argon at full level in the chamber. Next beyond the argon filter 24 is a sulfur filter 28, which is formed by pouring molten sulfur of high purity into a thin aluminum can and sealing the can to prevent leakage even if the sulfur melts during high power-level runs. In an enlarged outer portion 30 of the tube 14, an annulus 31 supports a plurality of aluminum filter element discs 32, positioned outward of the sulfur filter. A thin sheet 34 of thermal neutron absorbing material, such as cadmium or lithium, is positioned at the outer end of the filter series. A lead ring 35 fits closely up against the thermal neutron filter 34 to reduce the leakage of radiation around the filter. Further reduction in gamma radiation is achieved by placing a bismuth filter 38 closely adjacent to the reactor core 16.

The invention will now be described in greater detail by way of specific examples:

EXAMPLE 1

The Georgia Institute of Technology research reactor is fitted with a filter system. The reactor is a 93 percent enriched $U^{235}$, heavy water-moderated reactor with a maximum power level of 5 MW. A beam port designated H-12 is selected for the experiment because it is the largest diameter (15.1 cm) tangential port available. A 61 cm thick graphite plug scatters the neutron down the tangential tube to the filters which are placed approximately half-way between the core and the outer boundary of the biological shielding.

The filter system consists of, in order from the inner end outward, a 0.02 cm boron filter, a 77 cm liquid argon filter, a 15 cm sulfur filter, a 10 cm aluminum filter (four 2.5 cm discs) and an 0.08 cm cadmium filter.

With the reactor operating at a maximum capacity (5 MW) and emitting a flux of neutrons with wide energy distribution, the incident flux (n/cm$^2$ sec.) at the port is $110 \times 10^6$ at energies below 30 KeV and $1.9 \times 10^6$ at energies below 30 KeV. The incident neutron dose rate (rads/hr) is 216 at energies below 30 KeV and 8 at energies above 30 KeV. Thus fast neutrons make up only about 1.7 percent of the total flux and 3.6 percent of the total incident dose rate from the neutrons. The incident gamma dose rate is 55 rads/hr.

To be effective in destroying brain tumor, at least 2000 rads of which must be delivered by the $B^{10}(n,\alpha)$-$Li^7$ reaction. Assuming 100 ppm of $B^{10}$ in the tumor, and multiplying the incident epithermal flux by a factor of three to account for the buildup of the thermal flux from the incident epithermal flux, a 2 hour irradiation time is required. The total gamma dose of 110 rads in a two hour period is within the medically acceptable limit for a single dose, i.e., less than 750 rads.

This example shows that with a filter system according to the present invention, a neutron beam of mixed energies can be effectively filtered to provide a beam of epithermal neutrons that is effective for BNCT and is reasonably safe.

EXAMPLE 2

The effectiveness of using an epithermal beam to provide a high thermal neutron flux below the surface of a head is demonstrated by the following experiment.

The reactor port used in Example 1 is fitted with a filter system consisting of 0.18 cm boron, 21.6 cm Al, 25.4 cm S, and 0.08 cm Cd filters. A 15 cm diameter polyethylene head phantom is used to simulate body tissues, and measurements of flux are made with the activation of indium foils. The phantom head is positioned 50 cm from the beam port.

The measured epicadmium flux (above 1.0 eV) and thermal flux (below 1.0 eV and predominantly below 0.5 eV) are shown on the semilog graph in FIG. 4, the flux being shown on the ordinate and the depth of the foils in the phantom head being shown on the abscissa. The measured thermal flux may be considered generally accurate; however, due to an artifact of measurement, the epicadmium flux (broken line) is skewed in the nonlinear area (below about 3 cm). In this region, an extrapolation (dot-dash) to 0 cm depth is a more accurate representation of the epicadmium flux. As the epicadmium neutrons penetrate, they are moderated by the polyethylene into thermal flux. The thermal flux peaks at a depth of about 3 cm, and a generally maximum thermal flux is maintained as far as 8 or 9 cm. into the phantom head.

This experiment shows that by using a beam of primarily epithermal neutrons, obtained by filtering mixed energy radiation through an aluminum-sulfur filter, a low thermal flux is provided at the surface while a high thermal flux is provided inward of the surface at depths where brain tumors are frequently found, making the non-invasive treatment of such a tumor possible.

While a radiation beam having neutrons predominantly in the epithermal range is preferable for deep-seated tumors, a thermal neutron beam may be most effective for surface tumors. However, an epithermal beam may be used to treat a surface tumor by increasing the effective depth of the tumor by covering the surface tumor with a sheet of polymeric material, such as polyethylene.

The invention provides the means of fulfilling the promise of neutron-capture therapy for patients having malignant tumors. The beam provided by the radiation filter system of the invention is predominantly comprised of neutrons having energies that penetrate to typical depths of tumors without being absorbed by and damaging outer tissues and having energies sufficiently low that they are moderated by the outer tissues to thermal neutrons for capture by isotopes in the tumor. With a gamma radiation filter, a high neutron flux is provided without excessive gamma radiation.

While the invention has been described in terms of a preferred embodiment, modifications may be made that are obvious to one with ordinary skill in the art. For example, rather than using a beam tube tangent to the reactor core for irradiation, a beam tube radial to the core 10 can be used with thicker argon filters to remove the larger gamma radiation flux found in a direct beam. The greater neutron dose rate provided by direct irradiation shortens the treatment period providing increased patient comfort. While the thicknesses of the filters in the beam direction have been described for use with a particular neutron source, i.e., the reactor at Georgia Tech, it is to be understood that the filter sizes will be varied according to the intensity and energy distribution of the particular neutron source.

Various features of the invention are set forth in the following claims.

What is claimed:

1. A filter system for a radiation beam comprising an assemblage of filters selected from the group consisting of (A) an aluminum filter plus a sulfur filter, (B) an aluminum filter plus an argon filter, (C) a sulfur filter plus an argon filter, and (D) an aluminum filter plus a sulfur filter plus an argon filter, said filter system selectively transmitting neutrons having energies below 30 KeV, whereby said filter system attenuates a radiation beam with neutrons having an energy distribution extending throughout the thermal, epithermal and fast neutron ranges to produce an attenuated beam with an energy distribution particularly useful in neutron-capture tumor therapy.

2. A filter system according to claim 1 also including a thermal neutron filter means for reducing the proportion of neutrons having energies below 0.5 eV in the attenuated beam.

3. A filter system according to claim 2 wherein said thermal neutron filter means includes a first neutron filter that is positioned inward of said assemblage of filters to substantially eliminate the production of gamma radiation by thermal neutrons in said assemblage of filters.

4. A filter system according to claim 3 wherein said thermal neutron filter means further includes a second neutron filter means positioned outward of said assemblage of filters.

5. A filter system according to claim 1 also including a gamma ray shield formed of a material selected from the group consisting of lead and bismuth.

6. In combination, means for providing a beam of neutrons having energies distributed through the thermal, epithermal and fast neutron ranges and a filter system means for attenuating said beam of neutrons to provide an attenuated beam of neutrons with an energy distribution particularly useful in neutron-capture tumor therapy, said filter system means comprising an assemblage of filters selected from the group consisting of (A) an aluminum filter plus a sulfur filter, (B) an aluminum filter plus an argon filter, (C) a sulfur filter plus an argon filter and (D) an aluminum filter plus a sulfur filter plus an argon filter.

7. A combination in accordance with claim 6 wherein said filter system means include in addition to said assemblage of filters a thermal neutron filter means for reducing the proportion of neutrons having energies below 0.5 eV in the attenuated beam.

8. A combination in accordance with claim 7 wherein said thermal neutron filter means includes a first neutron filter that is interposed in said beam of neutrons before said assemblage of filters, whereby generation of gamma radiation by thermal neutrons in said assemblage of filters is minimized.

9. A combination in accordance with claim 8 wherein said thermal neutron filter means further includes a second neutron filter means positioned outward of said assemblage of filters.

10. A combination in accordance with claim 6 wherein said filter system means include, in addition to said assemblage of filters, gamma radiation shield means for reducing the gamma radiation in the attenuated beam.

11. In combination, a nuclear reactor having a port through which a radiation beam is emitted, and a filter system for a radiation beam comprising an assemblage of filters selected from the group consisting of (A) an aluminum filter plus a sulfur filter, (B) an aluminum filter plus an argon filter, (C) a sulfur filter plus an argon filter, and (D) an aluminum filter plus a sulfur filter plus an argon filter, said filter system selectively transmitting neutrons having energies below 30 KeV, whereby said filter system attenuates a radiation beam with neutrons having an energy distribution extending through the thermal, epithermal and fast neutron ranges to produce an attenuated beam with an energy distribution particularly useful in neutron-capture tumor therapy.

12. A combination according to claim 11 wherein said filter system also includes a thermal neutron filter means for reducing the proportion of neutrons having energies below 0.5 eV in the attenuated beam.

13. A combination in accordance with claim 12 wherein said thermal neutron filter means includes a first neutron filter that is interposed in said beam of neutrons before said assemblage of filters, whereby generation of gamma radiation by thermal neutrons in said assemblage filters is minimized.

14. A combination in accordance with claim 13 wherein said thermal neutron filter means further includes a second neutron filter means positioned outward of said assemblage of filters.

* * * * *